United States Patent [19]

De Vincentiis

[11] 4,431,664

[45] Feb. 14, 1984

[54] COMPOUND WITH ANTIULCEROGENIC ACTIVITY, PROCESS FOR THE PREPARATION THEREOF AND PHARMACEUTICAL COMPOSITION THEREFROM

[75] Inventor: Leonardo De Vincentiis, Rome, Italy

[73] Assignee: Ausonia Farmaceutici s.r.l., Pomezia, Italy

[21] Appl. No.: 405,332

[22] Filed: Aug. 5, 1982

[30] Foreign Application Priority Data

Aug. 18, 1981 [IT] Italy ................................ 23546 A/81

[51] Int. Cl.$^3$ ..................... C07D 317/44; A61K 31/36
[52] U.S. Cl. ..................................... 424/282; 549/335; 549/440
[58] Field of Search .................... 549/435; 424/282

[56] References Cited

U.S. PATENT DOCUMENTS 4,140,681 2/1979 Okamoto et al. .................... 549/435

FOREIGN PATENT DOCUMENTS 159936 5/1952 Australia ............................. 549/435

Primary Examiner—Ethel G. Love
Attorney, Agent, or Firm—Walter H. Schneider

[57] ABSTRACT

The present invention relates to a new compound with antiulcerogenic activity, and precisely N-(2-(((5-dimethylamino)-methyl-2-furanyl)-methyl)-thio)-ethyl)-N'-(3,4-methylendioxybenzyl)-2-nitro-1,1-ethenediamine, of formula (I):

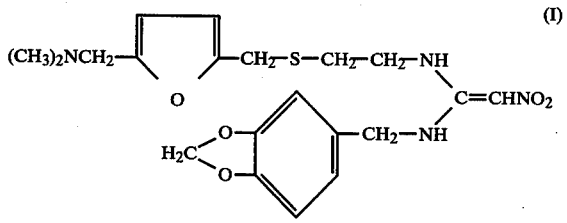

5 Claims, No Drawings

COMPOUND WITH ANTIULCEROGENIC ACTIVITY, PROCESS FOR THE PREPARATION THEREOF AND PHARMACEUTICAL COMPOSITION THEREFROM

The invention relates also to a process for the preparation of (I), characterized in that 2-((2-aminoethyl)thio-methyl)-5-(dimethylaminomethyl)-furan (II) is reacted with 1-nitro-2-methylthio-2-(3,4-methylenedioxybenzylamino)-ethene (III), according to the following reaction scheme:

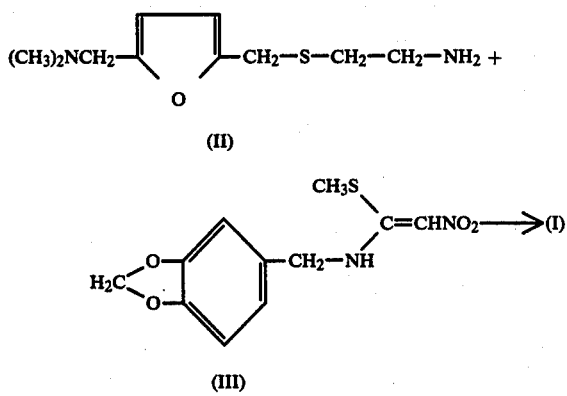

The reaction is carried out in aprotic solvents, such as chlorinated hydrocarbons, at temperatures ranging from 30° to 120° C., suitably from 50° to 100° C., as long as methylmercaptan developes.

1-Nitro-2-methylthio-2-(3,4-methylendioxybenzylamino)-ethene (II) can be obtained by condensation of 4,4-methylenedioxy-benzylamine (IV) with 1-nitro-2,2-di(methylthio)-ethene (V):

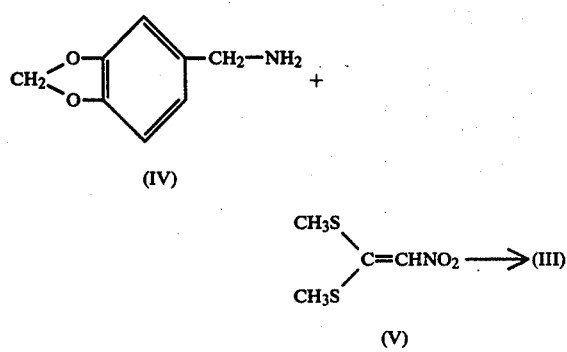

The compound of formula (I) shows a very high antiulcerogenic activity, substantially higher than that of very well known compounds having analogue structure, such as cimetidine and ranitidine. With respect to the latter compounds, compound (I) shows another advantage that is a more long lasting pharmacological effect.

Compound (I) has a very low acute toxicity, both in mouse and in rat: the $LD_{50}$ values per os are respectively higher than 3.000 and 5.000 mg/kg.

Therefore, the present invention relates also to pharmaceutical compositions with antiulcerogenic activity, containing compound (I) as the active ingredient.

The following example illustrates the process according to the invention, but is not limitative of the invention.

EXAMPLE (a) 1-Nitro-3-methylthio-2-(3,4-methylenedioxybenzylamino)-ethene (III)

16.1 Grams of 1-nitro-2,2-dimethylthio-ethene (V) were dissolved in 100 ml of refluxing 1,1,2-trichloroethene; to the so obtained homogeneous solution 7.5 g of 3,4-methylenedioxybenzylamine (III), dissolved in 40 ml of the same solvent, were added during 30 minutes.

The reaction mixture was refluxed for two and a half hours, the solvent was then evaporated under reduced pressure, the residue was purified by chromatography on silica gel column, eluting with petroleum ether and then with dichloromethane. The so obtained product was crystallized from dichloromethane and diethyl ether.

M.p. 118°–119° C.

(b) N-(2-(((5-(dimethylamino)-methyl-2-furanyl)-methyl)-thio)-ethyl)-N'-(3,4-methylenedioxybenzyl)-2-nitro-1,1-ethendiamine (I)

To 10 grams of compound (III), dissolved in 100 ml of 1,1,2-thricloroethene, 12 g of 2-(aminoethyl-thiomethyl)-5-(dimethylamino-methyl)-furan were added. The reaction mixture was refluxed for 6 hours, the solvent was then evaporated, and the residue was treated with diethyl ether.

The obtained precipitate was isolated by filtration, dissolved in ethanol and again precipitated by adding water. The product was recrystallized from ethanol-water.

M.p. 98°–102° C.

Elemental analysis: for $C_{20}H_{26}N_4O_5S$ (PM=434,506). Calc.%: C=55.29; H=5.99; N=12.90. Found.%: C=55.44; H=6.07; N=12.81.

NMR spectrum confirms the structure of the product (internal standard TMS; solvent DMSO): 2.1 δ, s, 6H, $(CH_3)_2N$; 2.7 δ, m, 4H, $N-CH_2-CH_2-S$; 3.4 δ, s, 2H, furyl—$CH_2$—S; 3.7 δ, d, 2H, phenyl—$CH_2$—S; 3.85 δ, s, 2H, furyl—$CH_2$—S; 4.3 δ, s, 2H, $O-CH_2-O$; 6–7 δ, m, 6H, aromatic+$CHNO_2$; 8 and 10 δ, broad s, 2H, NM.

According to well known methods, the addition salts of compound (I) with pharmaceutically acceptable organic or inorganic acids have been prepared, particularly with hydrochloric, citric, maleic and tartaric acid. As mentioned hereinabove, compound (I)—which from now on will be defined also with the code name AP 880 for sake of shortness—proved to be endowed with a high antiulcerating activity, as well as with a substantially lower toxicity than the one exerted by pharmaceuticals having analogue structure, as shown by the experimental results hereinabove. In the toxicity and activity tests reported herein, AP 880 was used in the form of citrate.

TOXICITY

The toxicity of AP 880 by single administration has been studied in comparison with the toxicity of ranitidine in mouse, by administration of larger and larger doses of compound (I) by the intraperitoneal route. The $LD_{50}$ values, determined according to the method of Litchfield and Wilcoxon (J. Pharm. Exp. Ther. 96–99, (1949)) are reported in the following Table:

TABLE

| Species | Administration route | LD$_{50}$ (mg/kg) AP 880 | LD$_{50}$ (mg/kg) Ranitidine |
|---|---|---|---|
| Mouse | i.p. | 3.500 | 2.100 |

A substantially lower toxicity of AP 880 is shown with respect to the one of ranitidine as regards the administration route and the experimental conditions employed.

GASTROPROTECTIVE ACTIVITY

The gastroprotective activity of AP 880 with respect to ranitidine at equimolecular doses has been tested in the rat according to the test of ulcera induced by "immersion stress".

Male Wistar rats have been used weighing 240–260 g and kept fasted from 18 hours. Immediately after the administration of the tested compounds by the oral route, the animals were immobilized in a cage suited to provoke the stress, according to the method of Takagi et al.; then the cage was immersed upright in a water bath at 23±1° C. for seven hours up to the height of the xiphoid process. Subsequently, the stomachs were removed and the area of lesion of the same stomachs was calculated in order to determine an index of lesion. The gastroprotective activity of the compounds was determined on the basis of the ED$_{50}$ which, after comparison with the results, proved to be 25 mg/kg for both the tested compounds.

ANTIULCERATING ACTIVITY

The evaluation of the activity of AP 880 for this experimental pattern was determined in the rat according to the Shay ulcera test, by comparison of the tested compound with ranitidine at equimolecular doses. Male Wistar rats weighing 220–240 g, fasted from 48 hours, were kept in single cages having the bottom of wide-mesh wire-net. The pylorus of the ether-anaesthetized rats was bound and the compounds were immediately administered by the intraperitoneal route.

Eighteen hours after the treatment the animals were killed and their stomachs were removed in order to determine the perforation index. The ulcerous symptomatology of the gastric mucosa was evaluated by means of an index for the evaluation of the lesions. From the obtained results, the ED$_{50}$ was determined, which is 50 mg/kg for both the tested compounds in the employed experimental conditions.

I claim:

1. N-(2(((5-dimethylamino)-methyl-2-furanyl)-methyl)-thio)-ethyl)-N'-(3,4-methylenedioxybenzyl)-2-nitro-1,1-ethenediamine of formula (I)

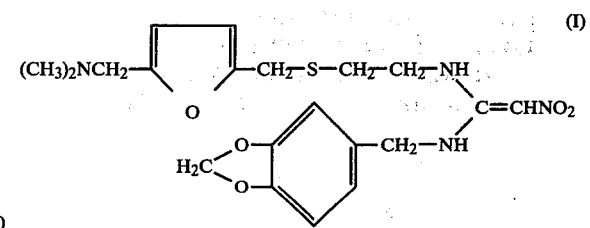

and their addition salts with pharmaceutically acceptable inorganic or organic acids.

2. Process for the preparation of compound (I), in which 2-((2-aminoethyl)thio-methyl)-5-(dimethylamino-methyl)-furan (II) is reacted with 1-nitro-2-methylthio-2-(3,4-methylenedioxybenzylamino)-ethene (III), according to the following reaction scheme:

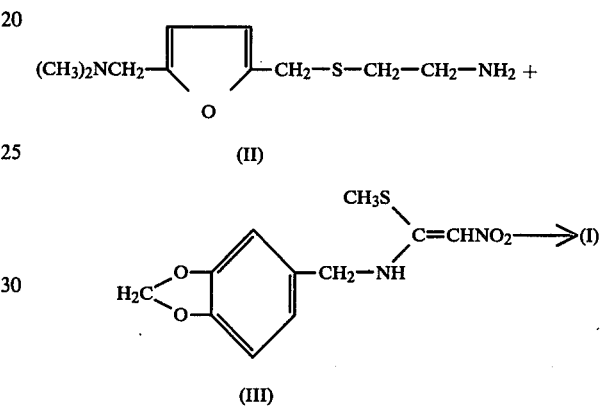

3. Process according to claim 2, in which the reaction is carried out at temperature ranging from 30° to 120° C., preferably from 50° to 100° C.

4. Process according to claims 2 and 3, in which the reaction is carried out in aprotic solvents, preferably in chlorinated hydrocarbons.

5. Pharmaceutical composition with antiulcerogenic activity, which contains an antiulcerogenic effective amount of N-(2-(((5-dimethylamino)-methyl-2-furanyl)-methyl)-thio)-ethyl)-N'-(3,4-methylenedioxybenzyl)-2-nitro-1,1-ethenediamine of formula (I):

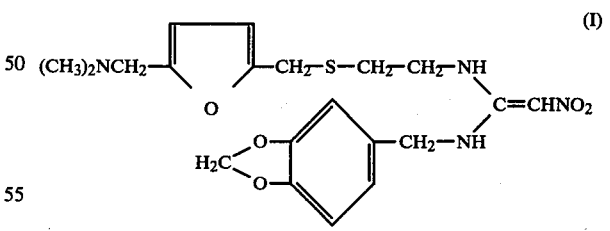

or their addition salts with pharmaceutically acceptable inorganic or organic acids, as the active ingredient.

* * * * *

UNITED STATES PATENT AND TRADEMARK OFFICE
CERTIFICATE OF CORRECTION

PATENT NO. : 4,431,664
DATED : Feb. 14, 1984
INVENTOR(S) : Leonardo De Vincentiis It is certified that error appears in the above-identified patent and that said Letters Patent are hereby corrected as shown below:

Col. 1, before the first paragraph, the following paragraph should appear:

---The present invention relates to a new compound with antiulcerogenic activity, and precisely N-(2-(((5-dimethylamino)-methyl-2-furanyl)-methyl)-thio)-ethyl)-N'-(3,4-methylenedioxybenzyl)-2-nitro-1,1-ethenediamine of formula I:

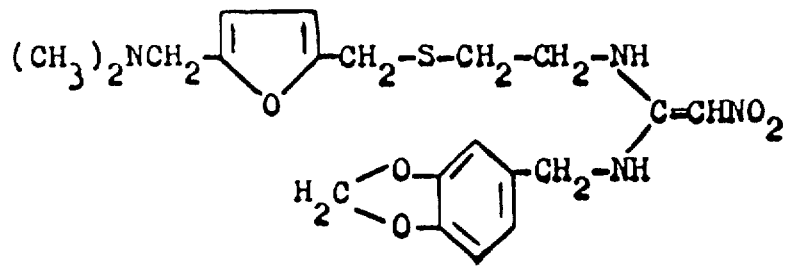

(I)

Signed and Sealed this

Twenty-fifth Day of June 1985

[SEAL]

Attest:

DONALD J. QUIGG

Attesting Officer     Acting Commissioner of Patents and Trademarks